US00PP12718P2

(12) United States Plant Patent
Saul

(10) Patent No.: US PP12,718 P2
(45) Date of Patent: Jun. 25, 2002

(54) *STOKESIA LAEVIS* PLANT NAMED 'COLORWHEEL'

(76) Inventor: Robert Mark Saul, 940 Carter Dr., Atlanta, GA (US) 30319

( * ) Notice: Subject to any disclaimer, the term of this patent is extended or adjusted under 35 U.S.C. 154(b) by 15 days.

(21) Appl. No.: 09/710,790

(22) Filed: Nov. 13, 2000

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Anne Marie Grünberg

(57) ABSTRACT

A new and distinct variety of Stokesia plant named 'Colorwheel', characterized by its unique display of flower colors, numerous flowers per plant, increased growth rate, and attractive semi-evergreen foliage.

1 Drawing Sheet

BACKGROUND OF THE INVENTION

The present invention relates to a new and distinct variety of Stokesia plant, botanically known as *Stokesia laevis* and a member of the composite family. This new Stokesia variety, hereinafter referred to as 'Colorwheel', was discovered by Robert M. Saul in the summer of 1997 as an openly pollinated seedling of an unidentified selection of *Stokesia laevis* at Saul Nurseries, Inc. in Dahlonega, Ga. The value of this new cultivar lies in its unique display of flower colors, numerous flowers per plant, increased growth rate and attractive semi-evergreen foliage.

Asexual propagation of the new plant by division has been under Mr. Saul's direction at the same location. Several generations of the new plant have been evaluated and the distinctive characteristics of the plant have remained stable. The plant cannot be reproduced true from seed.

SUMMARY OF THE INVENTION

The following are the most outstanding and distinguishing characteristics of this new cultivar when grown under normal horticultural practices in Dahlonega, Ga.

1. Attractive large flowers are initially white and with further development transform to a dark purple while retaining the white center.
2. Numerous flowers per plant.
3. Fast growth rate under normal fertilization and moisture conditions.
4. Easily propagated by division.
5. Heat and drought resistant.
6. Tolerates full sun to part shade.
7. Desirable in planters.
8. Desirable as a cut flower.
9. Effectively used in mass in perennial gardens.
10. Hardy to Zone 6.
11. Semi-evergreen in Zones 7–9.

DESCRIPTION OF THE DRAWINGS

This new variety of *Stokesia laevis* is illustrated by the accompanying photographic prints in which.

1.

2.

Figure 1:
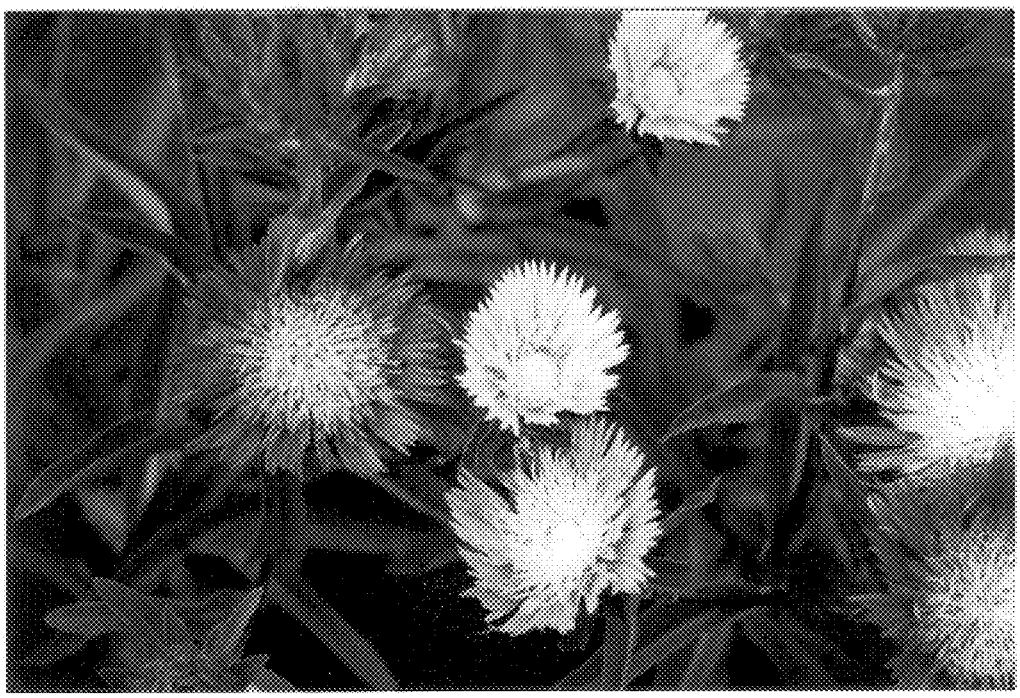
FIG. 1 is a close-up showing flower, foliage, and stem color as well as flower size and form.
Figure 2:
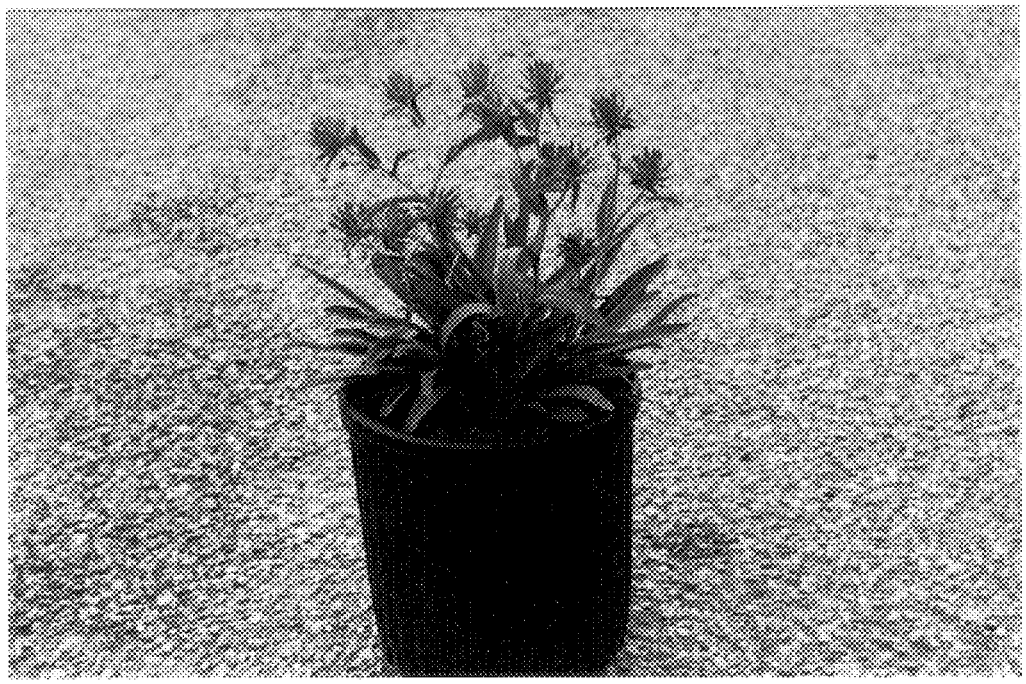
FIG. 2 shows the growth habit of a young three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Stokesia based on my observations of plants grown in wholesale commercial production practices, in greenhouses, and in established landscape plantings in Dahlonega, Ga.

Distinctive Characteristics:

| Characteristic | *Stolesia I.* 'Colorwheel' | *Stolesia I.* 'Purple Parasols' | *Stolesia I.* (The Species) |
|---|---|---|---|
| Height (Mature) | 8–10" | 8–10" | 8–10" |
| Width (Mature) | 24–26" | 24–26" | 24–26" |
| Bloom Height | 12–24" | 12–26" | 12–24" |
| Leaf Length | 6–10" | 6–10" | 6–10" |
| Bloom Period | Spring–Fall | Spring–Fall | Spring–Fall |
| Flower Diameter | 2–4" | 2–4¾" | 2–3" |
| Flower Color | White–Light Purple–Dark Purple (White Center) | Light Blue–Dark Blue–Purple–Dark Hot Pink | Blue–Purplish Blue |

Stokesia 'Colorwheel' can be compared to the patented plant Stokesia 'Purple Parasols', U.S. Plant Pat. No. 10,660, and the species *Stokesia laevis*, however, in side-by-side comparisons conducted in Dahlonega, Ga., the flower colors of these plants differed greatly as indicated above.

Classification

Botanic: *Stokesia laevis* 'Colorwheel'.
Commercial: Herbaceous perennial.
Form: Foliage dense and mounding. Inflorescences are erect and borne above the foliage.

Height: Foliage 8 to 10". Blooms 12 to 24".
Width: 24 to 26".
Size: In a period of four to five months from a division, the plant reaches a saleable size of 6 to 8" in a 3 quart container. Blooms begin to appear at this time and are held above the foliage at about 12".
Foliage: Basal, simple, semi-evergreen, thick, glandular-punctate, oblong-lanceolate to spatulate and varying in size from 6 to 10" long and 1 to 2" wide. The margins are entire, apex acute, base cuneate to attenuate and the petiole is ¼ to ½" long. Midveins are impressed on the upper surface and prominent on the underside. The upper surface of the immature leaves is dull, glabrous, and Green Group 138A and the underside is Green Group 138B and matte. The upper surface of the mature leaves is Green Group 137A, dull and glabrous. The underside is Green Group 137C and matte. Midveins are Yellow-Green Group 145C top and bottom. Petioles are Yellow-Green Group 145C overlaid with Greyed-Purple Group 187D. The alternate stem foliage is similar to the basal foliage, however, it is reduced upward to 1 to 2½" long and ¼ to ½" wide, becoming sessile, clasping, and spinulose-dentate near the base of the leaf.

Like the parent species, 'Colorwheel' has a uniform mounding plant habit. It grows by adding bibs or small clumps of leaves on short rhizomes on the side of the existing clump. The rhizomes are normally less than one inch long. As the plant grows, the clump becomes larger, 24 to 26" wide, and can be propagated by division. The root system is fibrous.

In 1999, the date of initial spring growth was March 23, in Dahlonega, Ga. After the initial spring flush there was almost continuous growth until that fall ending October 12, also in Dahlonega, Ga. This growth pattern was identical to the parent species, however, 'Colorwheel' clumps increased in size quicker that the parent species.

Buds: There are 3 to 5 buds per inflorescence borne on 12 to 24" tall floccose, leafy stems (Yellow-Green Group 145C), arising from leaf axils and held above the foliage. These stems are ¼" diameter at base and ⅛" distally. The peduncle is 2 to 4" long, strong, erect, and wooly. The involucres are hemispheric, persistent, ½ to 1" long and ½ to 1" wide. The bracts are imbricate, Yellow-Green Group 151A, numbering from 20 to 30, outer bracts foliaceous, Green Group 137A, elliptic to lanceolate, to 1¼" long, spinulose-dentate near base, the inner bracts entire or erose, ciliate at apex and firm.

Flowers: Single, perfect, non-fragrant, radiate arranged in corymbs. The individual flowers are 2 to 4" across and consist of two series of ray flowers. The 15 to 30 outer ray florets are ½ to 1" long and ¼ to ½" wide, pleated at the base, enlarging at apex, and have 4 to 5 deeply cut lobes. There are 40 to 60 inner florets which are tubular, ½ to 1" long and 1/16 to ⅛" wide. The filaments are ⅜ to ⅝" long and White Group 155D. The anthers are ⅛" long, Brown Group 200D, and the pollen matures to White Group 155A. The pistil is ⅝" long and White Group 155D. The stigma is two-cleft and the ovary is Yellow-White Group 158A.

Flowering normally begins in May and continues through fall. Flowers last on the plant from 8 to 21 days and as a cut flower for about 12 days. A mature plant will produce from 25 to 50 blooms during the flowering season. It normally takes 2 to 3 days for the flower to open completely. Each bloom opens solid White Group 155D and changes progressively with time to a light lavender (Purple Group 76D), becoming darker each day until the final color of each flower is a deep Purple Group 77A. Intermediate bloom colors are Purple Group 76C, 76B, 76A, 78B, and 78A. As these blooms darken a characteristic 1 to 1½" diameter white center (White Group 155A) remains. While the first blooms are becoming darker, new white blooms are opening. This unique characteristic gives a multi-colored effect of blooms on the same plant.

Fruit: Achenes 3 to 4 angled, ⅛ to 3/16" long, 1/32 to 1/16" wide, and Grey-Brown Group 199C. The pappus is persistent. Normal fruit set is heavy.
Culture: Grows well in a wide range of conditions and tolerates sun to part shade. Grows in nearly any soil type, from moist to dry and sand to clay. Very heavy clays should be amended with peat moss, compost, or shredded pine bark to improve the soil texture. Poorly drained locations should be avoided. Responds well to mulching and medium appliations of fertilizer; prefers ph 6 to 7. Adaptable to containers and above ground planters. Propagated by division any time of year.
Pests: None serious.

I claim:

1. A new and distinct variety of Stokesia plant named 'Colorwheel', as described and illustrated.

* * * * *